(12) United States Patent
Wohlrab et al.

(10) Patent No.: US 8,568,748 B2
(45) Date of Patent: Oct. 29, 2013

(54) PHARMACEUTICAL FORMULATION COMPRISING CYCLOSPORIN AND USE THEREOF

(75) Inventors: Johannes Wohlrab, Halle/S. (DE); Reinhard Neubert, Halle/S. (DE); Konstanze Jahn, Beyendorf (DE)

(73) Assignee: JAGOTEC AG, Muttenz (CH)

( * ) Notice: Subject to any disclaimer, the term of this patent is extended or adjusted under 35 U.S.C. 154(b) by 1301 days.

(21) Appl. No.: 10/498,656

(22) PCT Filed: Dec. 14, 2001

(86) PCT No.: PCT/EP01/14749
§ 371 (c)(1),
(2), (4) Date: Dec. 17, 2004

(87) PCT Pub. No.: WO03/051385
PCT Pub. Date: Jun. 26, 2003

(65) Prior Publication Data
US 2005/0106189 A1 May 19, 2005

(51) Int. Cl.
*A61K 8/02* (2006.01)
*A61K 38/13* (2006.01)
*A61P 17/00* (2006.01)

(52) U.S. Cl.
USPC .................. 424/401; 514/18.6; 514/20.5

(58) Field of Classification Search
USPC ................ 424/401; 514/18.6, 20.5
See application file for complete search history.

(56) References Cited

U.S. PATENT DOCUMENTS

| | | | | |
|---|---|---|---|---|
| 5,589,455 | A * | 12/1996 | Woo | 514/11 |
| 5,614,491 | A * | 3/1997 | Walch et al. | 514/11 |
| 5,660,858 | A | 8/1997 | Parikh et al. | |
| 5,977,061 | A * | 11/1999 | Holy et al. | 514/7 |
| 6,190,692 | B1 * | 2/2001 | Busetti et al. | 424/451 |
| 6,809,077 | B2 * | 10/2004 | Or et al. | 514/11 |

FOREIGN PATENT DOCUMENTS

| | | |
|---|---|---|
| CA | 2164100 | 1/1995 |
| DE | 100 29 404 A1 | 1/2002 |
| EP | 0 760 237 A1 | 3/1997 |
| GB | 2 222 770 A | 3/1990 |
| HU | 223073 | 3/2004 |
| JP | 02-017127 | 1/1990 |
| JP | 02-121929 | 5/1990 |
| WO | WO 93/02664 | 2/1993 |
| WO | WO 94/08603 | 4/1994 |
| WO | WO 94/08605 | 4/1994 |
| WO | WO 97/22358 | 6/1997 |
| WO | WO 99/39700 | 8/1999 |
| WO | WO 0101960 A1 * | 1/2001 |

OTHER PUBLICATIONS

MedlinePlus: psoriasis [online] retrieved from http://www.nlm.nih.gov/MEDLINEPLUS/ency/article/000434.htm; retrieved on Aug. 27, 2008; 4 pages.*
Ezine Articles Acne Solutions [online] retrieved from the internet on Dec. 7, 2009 from: http://ezinearticles.com/?Acne-Solutions &id=146697; Feb. 16, 2006; 1 page.*
Moss Semin Neonatol 2000, 5, 311-320.*
Smith (Percutaneous Penetration Enhancers 1995, CRC Press LLC, p. 7).*
Hoang S. Tran, M.D., et al., *Site-Specific Immunosuppression using a New Formulation of Topical Cyclosporine A with Polyethylene Glycol-8 Glyceryl Caprylate/Caprate*; Journal of Surgical Research, vol. 83, No. 2, pp. 136-140 (May 15, 1999).
Vincent C.Y. Ho, M.D., FRCPC, et al., *Intermittent short courses of cyclosporine microemulsion for the long-term management of psoriasis: A 2-year cohort study*, J Am ACAD Dermatol, vol. 44, No. 4, pp. 643-651 (Apr. 2001).
Wolfgang Czech, M.D., et al., *A body-weight-independent dosing regimen of cyclosporine microemulsion is effective in severe atopic dermatitis and improves the quality of life*; J Am ACAD Dermatol, vol. 42, No. 4, pp. 653-659 (Apr. 2000).
Miriam Latterl, et al., *Pharmacokinetics of Cyclosporin Microemulsion in Patients with Inflammatory Bowel Disease*; Clin Pharmacokinet, vol. 40, No. 6, pp. 473-483 (2001).
A. Bhargava, et al., *Ocular Allergic Disease*, Drugs of Today vol. 34, No. 11, pp. 957-971 (1998).
Pharmaceutical Journal of Chinese People's Liberation Army, Apr. 2000, vol. 16, No. 2, pp. 88-90.
The Journal of Pharmaceutical Practice, vol. 18, 2000, No. 1, pp. 10-11.
S.S. Vojutskiu, "Kus Kolloidnoy Khimii", Moscow, Khimija, 1975, p. 404.

* cited by examiner

*Primary Examiner* — Blessing Fubara
*Assistant Examiner* — Kauser M Akhoon
(74) *Attorney, Agent, or Firm* — Marshall & Melhorn, LLC

(57) ABSTRACT

The present invention relates to a pharmaceutical formulation in colloidal form for topical application for the therapy and prophylaxis of pathological changes of the skin and/or integumentary structures of the skin and/or mucous membranes, including mucous membranes of the digestive tract, uro-genital tract and bronchial system and/or conjunctiva, containing a lipophilic phase in a quantity of 1-10% by weight, a mixture of surfactant and co-surfactant in a quantity of 1-50% by weight, a hydrophilic phase in a quantity of 40-80% by weight and, as active ingredient, cyclosporin and/or derivatives thereof in a concentration of 0.1-20% by weight.

7 Claims, 7 Drawing Sheets

Released pharmaceutical quantity (in %) as a function of time, $\bar{x} \pm s$, n=5

Released pharmaceutical quantity μg/10 mg applied formulation as a function of time

US 8,568,748 B2

PHARMACEUTICAL FORMULATION COMPRISING CYCLOSPORIN AND USE THEREOF

BACKGROUND OF THE INVENTION

The invention relates to colloidal pharmaceutical carrier systems, comprising cyclosporin, for topical application on skin and mucous membrane, comprising a surfactant/co-surfactant mixture (polyoxyethylene glycerol monooleate/poloxamers), a hydrophilic phase, e.g. propylene glycol/water mixtures, a lipophilic phase (isopropyl palmitate or oleic acid) and penetration enhancers.

This invention relates in particular to pharmaceutical formulations comprising cyclosporin A (CsA) for topical application for the therapy of pathological changes of the skin, integumentary structures of the skin or the mucous membranes, in particular atopical dermatitis and psoriasis vulgaris, the use of these formulations and a method for production thereof.

It is known that CsA is a cyclic peptide comprising 11 amino acids, with a molar mass of 1202 g/mol, which is produced from the soil fungus tolypocladium inflatum. CsA is soluble in water only with great difficulty (<0.04 mg/ml at 25° C.), whereas it is readily soluble in oils and alcohols. Its immune-modulating effect is based on inhibiting the release of interleukin-1 from macrophages and of interleukin-2 from T-helper cells, which in turn activate cytotoxic T-precursor cells, from which the cytotoxic T-cells arise. The transcription of the genes which encode the mentioned cytokines is hereby inhibited. CsA only thereby affects the naturally occurring body defence to a small extent. From a galenic point of view, the pharmaceutical is a substance which is particularly unsuitable for topical therapy because the high lipophily makes penetration through the epidermal lipid barrier appear virtually impossible. There is indicated as a reason for the failure of previous attempts at production and application of different lipophilic, hydrophilic and liposomal preparations for topical application, generally inadequate penetration of the pharmaceutical.

In dermatology, CsA has proved to be particularly useful in systematic application for the treatment of severe psoriasis and atopical dermatitis. In addition, reports and studies exist with respect to the effectiveness after systemic application in the case of a multiplicity of further inflammatory dermatoses (e.g. dermatitis ulcerosa, lichen ruber, actinic reticuloid, disseminated granuloma annulare).

In WO 9302664, W/O microemulsions are described which contain a lipophilic phase (medium-chain triglycerides and a surfactant with a low HLB value in the ratio 5:1 to 1.5:1), an aqueous hydrophilic phase, a surfactant with a high HLB value and a water-soluble therapeutic agent.

GB 2222770 comprises microemulsion preconcentrates comprising CsA, a hydrophilic phase (propylene glycol or partial ether of low-molecular mono- or polyoxyalkane diols) (transcutol/glycofurol), a lipophilic phase (medium-chain triglycerides and a surfactant) (Cremophor RH 40). The systems are suitable for peroral application and improve the bioavailability compared with existing systems.

EP 760237 describes O/W microemulsions for water-insoluble pharmaceutically active substances such as CsA which are completely dissolved in the dispersed oil droplets. The systems comprise a $C_2$-$C_{20}$ substituted plant triglyceride, lecithin and another surfactant and a hydrophilic phase containing propylene glycol.

WO 97/22358 includes microemulsion preconcentrates with CsA, the pharmaceutical being dissolved in a system, comprising hydrophobic, (tocopherols or tocopherol derivatives) and hydrophilic components (propylene carbonate and polyethylene glycol with a molecular weight <1000) and also surfactant.

In WO 94/08603, WO 94/08605 and WO 99/39700, pharmaceutical formulations are described which cite cyclosporin and derivatives thereof as possible active ingredient in the colloidal system.

The previously described systems have however some substantial disadvantages. For solubilisation, partly organic solvents are used which must be removed subsequently again from the formulation without leaving any residue. Often, surfactant/co-surfactant combinations for improving the solubility of the pharmaceutical are used in too high concentrations (more than 20% m/m). Some publications mention systems which are not composed exclusively of skin-compatible ingredients. Some microemulsion preconcentrates are described, the actual structure of which is intended to be formed in situ only after application. Furthermore, the existing systems have much greater particle diameters.

SUMMARY OF THE INVENTION

It is therefore the object of the present invention to propose a new colloidal pharmaceutical carrier system which essentially comprises dermatologically tolerable ingredients, this pharmaceutical carrier system being intended at the same time to have relatively low surfactant/co-surfactant contents.

The object is achieved by using a pharmaceutical formulation in colloidal form containing a lipophilic phase in a quantity of 1-10% by weight, a mixture of surfactant and co-surfactant in a quantity of 1-50% by weight, a hydrophilic phase in a quantity of 40-80% by weight and an active ingredient, cyclosporin and/or derivatives thereof in a concentration of 0.1-20% by weight.

According to the invention, it is therefore proposed that the pharmaceutical formulation in colloidal form comprises four essential components. The pharmaceutical formulation according to the invention comprises hence a lipophilic phase, a mixture of surfactant and co-surfactant, a hydrophilic phase and cyclosporin as active ingredient in the concentrations indicated above.

DESCRIPTION OF THE PREFERRED EMBODIMENTS

Figure 1:
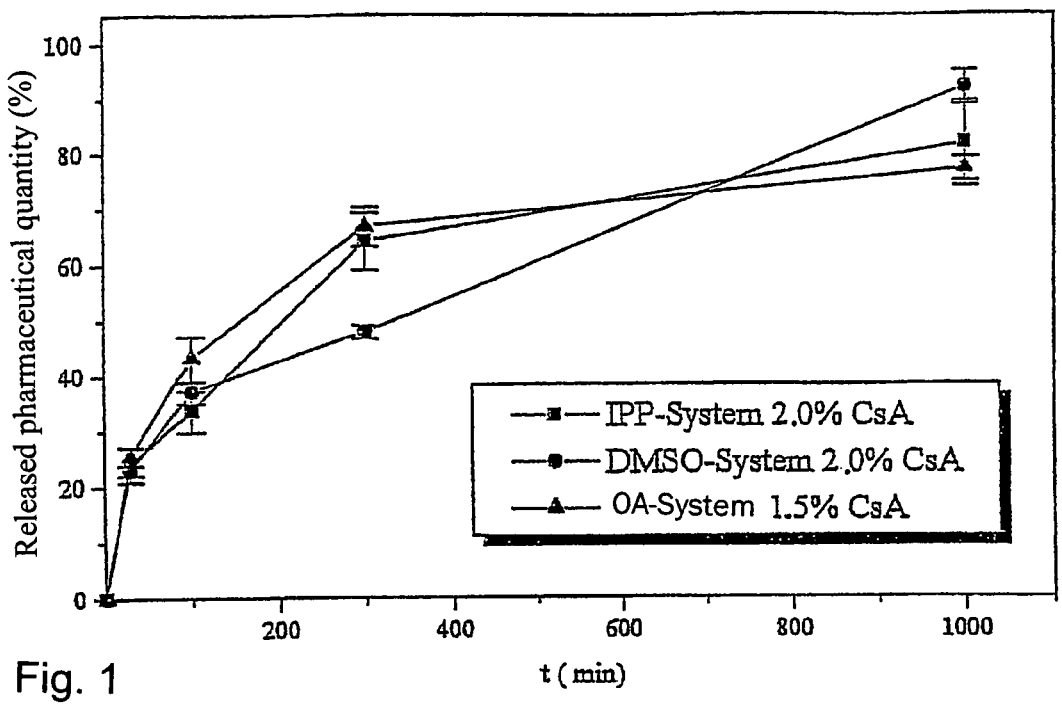
FIG. 1 shows the released pharmaceutical quantity (in %) as a function of time of composition according to the present invention.
Figure 2:
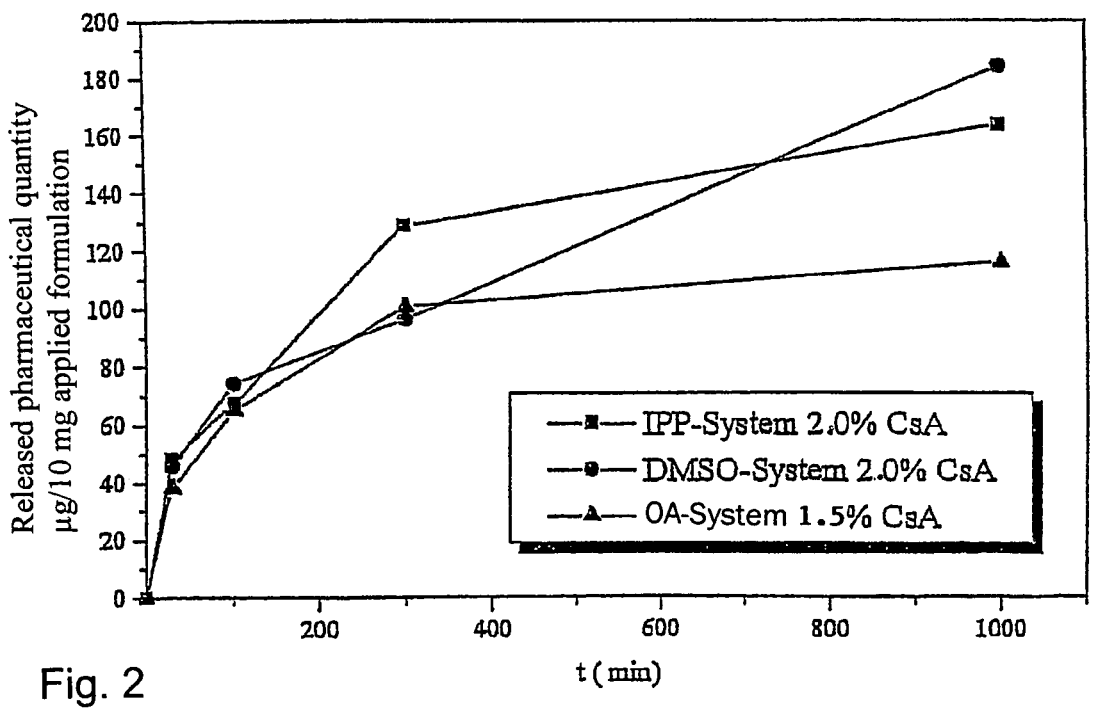
FIG. 2 shows a released pharmaceutical quantity μg/10 mg applied formulation as a function of time according to the present invention.
Figure 3:
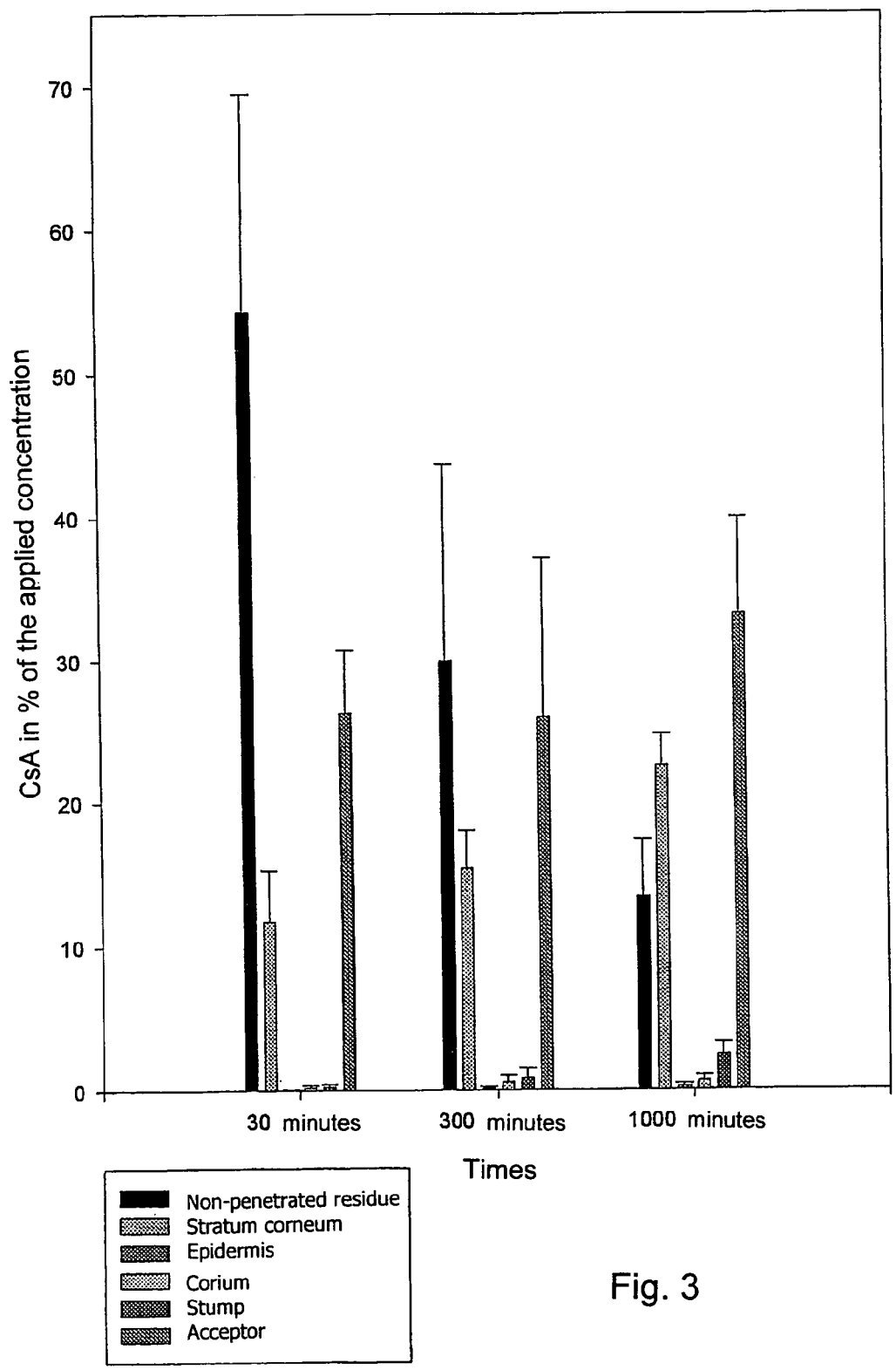
FIG. 3 shows a chart of CsA (in %) of the applied concentration versus time for a DMSO system.
Figure 4:
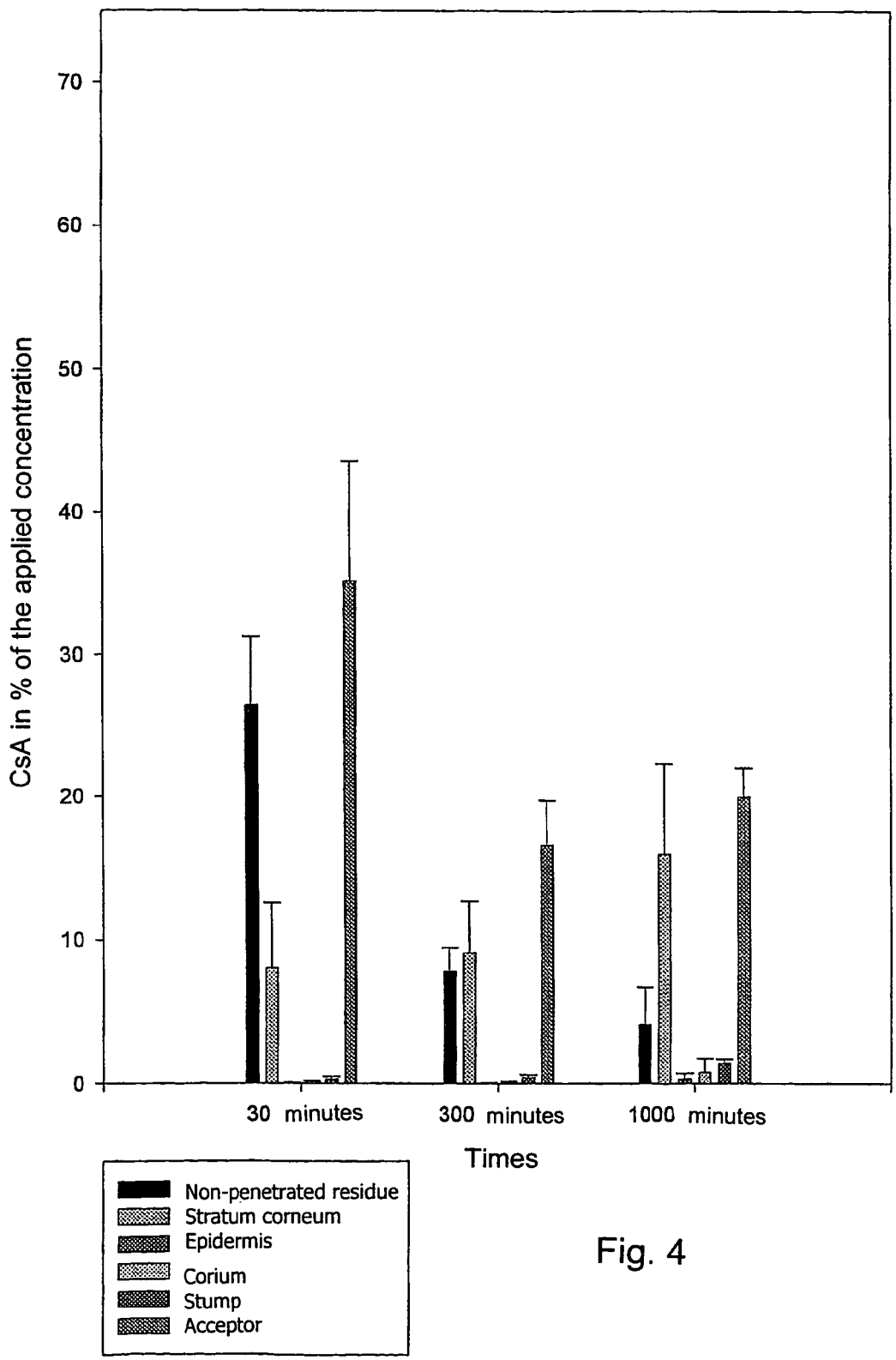
FIG. 4 shows a chart of CsA (in %) of the applied concentration over time for an IPP system.
Figure 5:
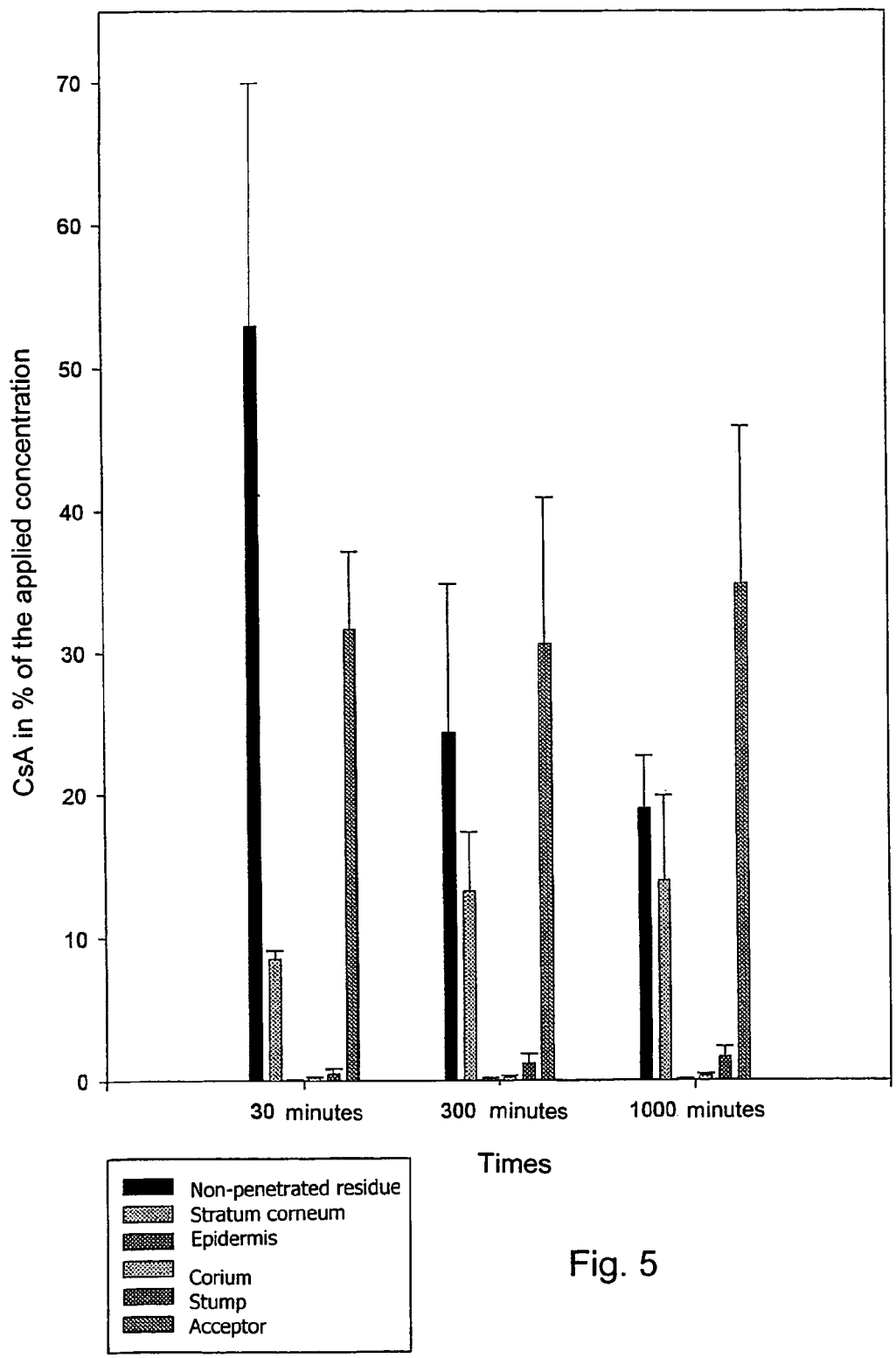
FIG. 5 shows a chart of CsA (in %) of the applied concentration against time for an OA system.
Figure 6:
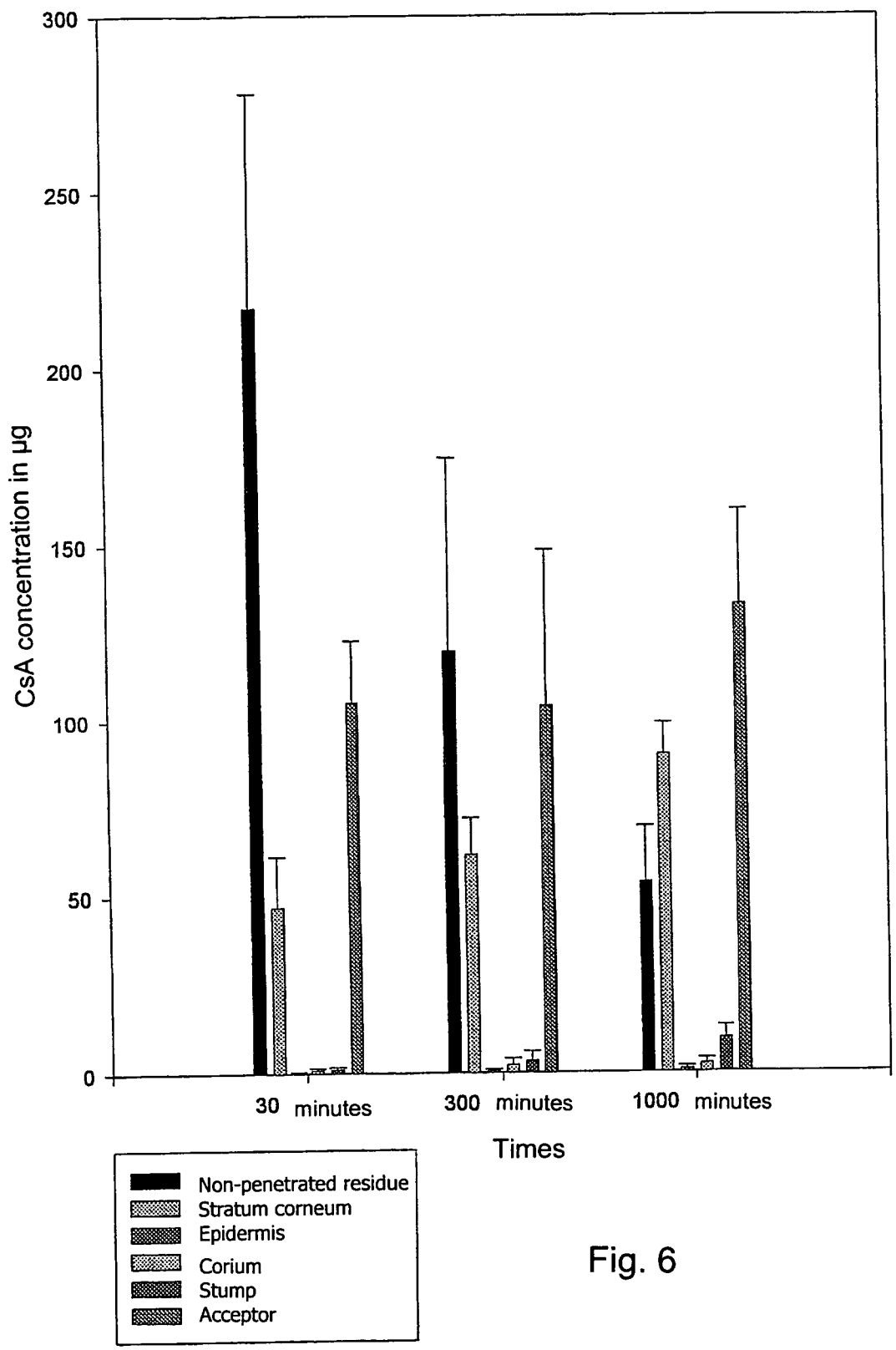
FIG. 6 shows a chart of CsA concentration (in μg) against time for a DMSO system.
Figure 7:
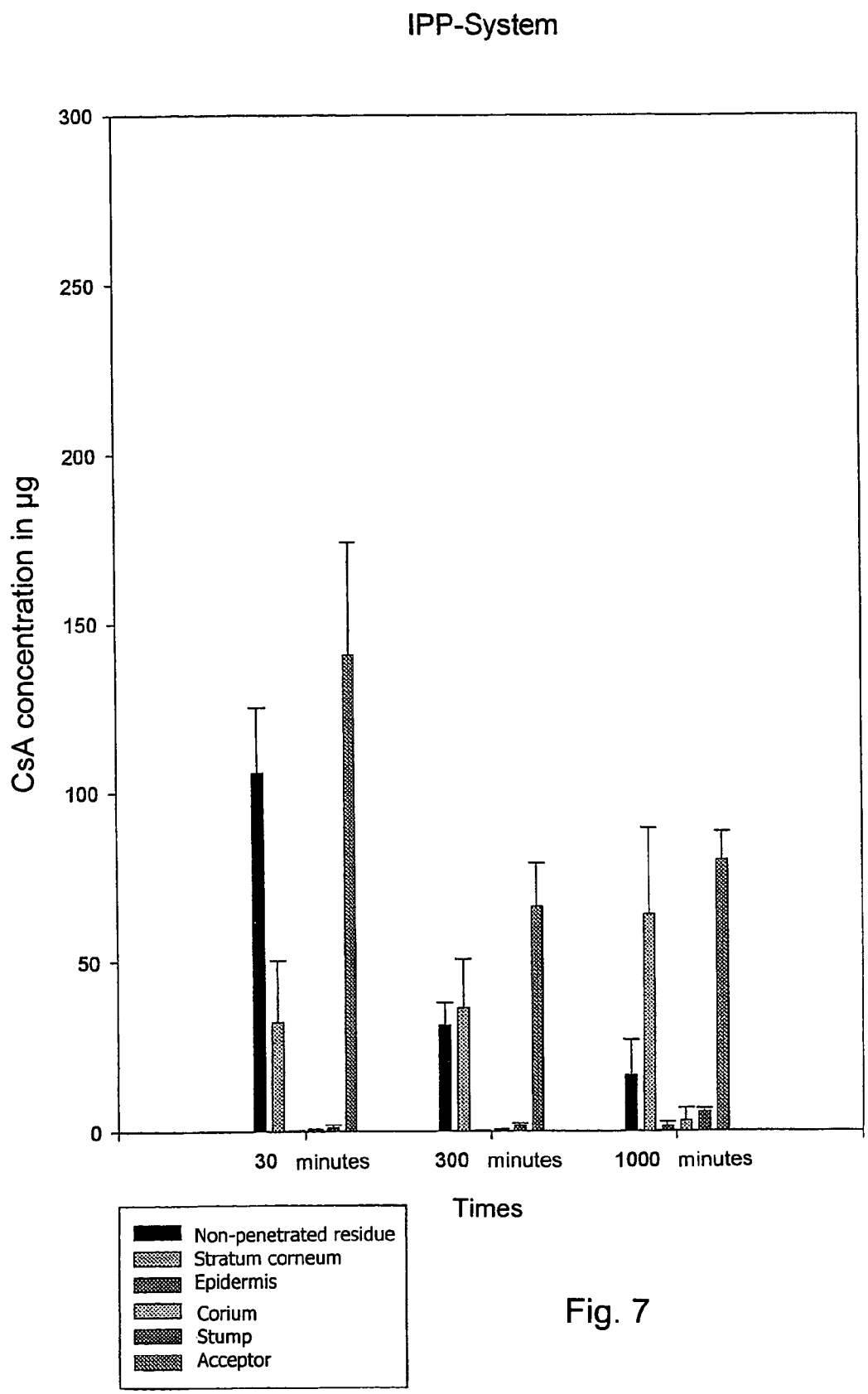
FIG. 7 shows a chart of CsA concentration (in μg) against time for an IPP system.
Figure 8:
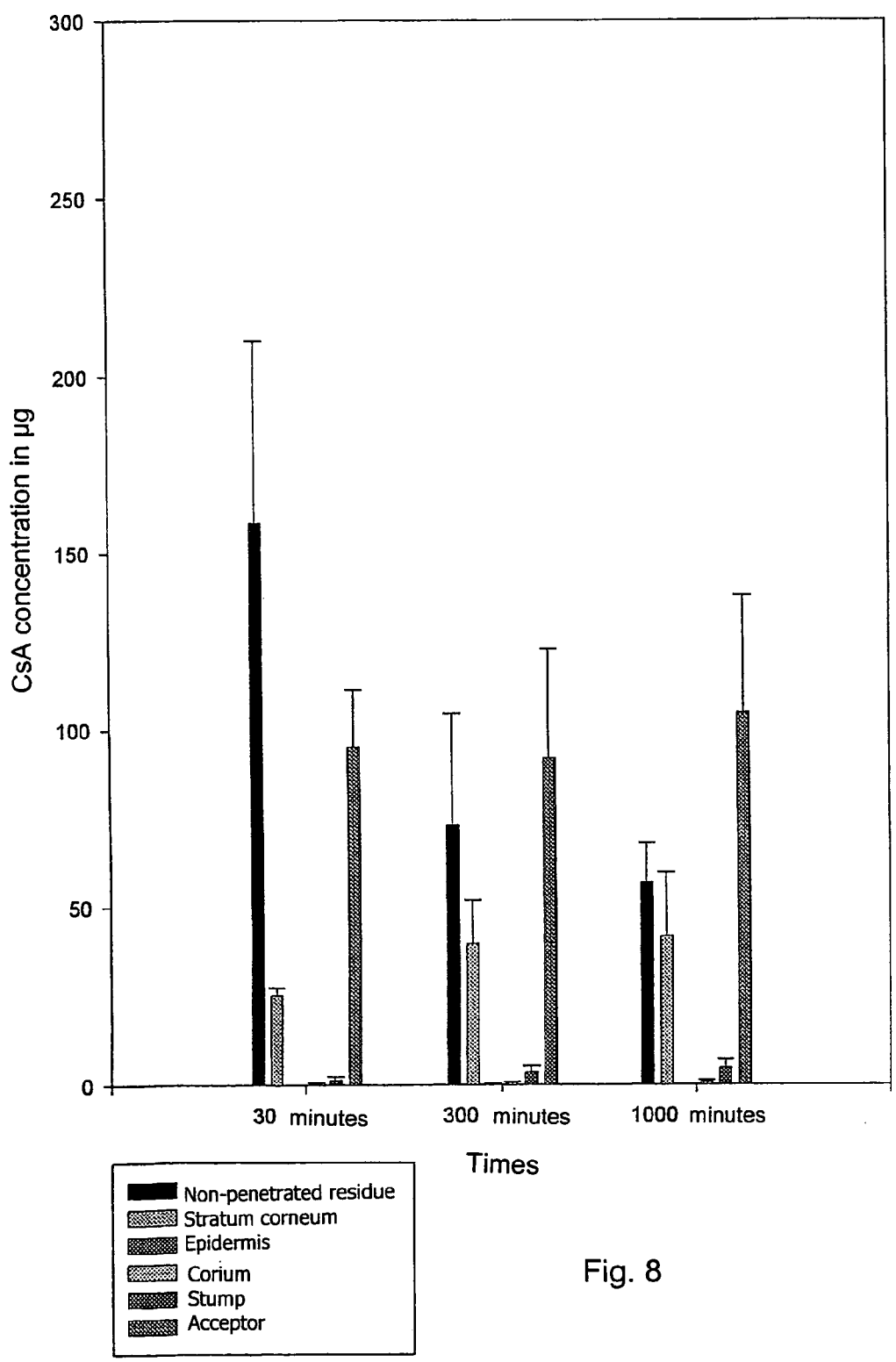
FIG. 8 shows a chart of CsA concentration (in μg) against time for an OA system.

The advantage of the colloidal pharmaceutical carrier systems according to the invention can be seen in particular in the composition of exclusively dermatologically tolerable ingredients, in relatively low surfactant/co-surfactant contents and also the small particle size of the dispersed particles.

From a material point of view, in particular oils, waxes or fats are particularly suitable for the lipophilic phase for the pharmaceutical formulation according to the invention. With respect to the lipophilic phase, all the lipophilic phases which are known per se to date from the state of the art can be used. Particularly preferred are triglycerides, isopropyl myristate, 2-octyldodecanol, isopropyl palmitate or oleic acid. The lipophilic phase is contained in the formulation with 1-10% by weight.

An essential element of the pharmaceutical formulation according to the invention is the mixture of surfactant and co-surfactant, which is used in a quantity of 1-50% by weight, preferably 20-30% by weight. From a material point of view, surfactants selected from polyoxyethylene glycerol fatty acid esters and polyoxyethylene sorbitan fatty acid esters are preferred. Examples of the co-surfactant are poloxamers, block copolymers of polyoxyethylene and polyoxyropylene.

A particularly preferred mixture ratio is a mass ratio of 1.5 to 2.5 for the surfactant and 2.5 to 3.5 for the co-surfactant. The inventors were able to prove that in particular maintaining this surfactant/co-surfactant mixture ratio is important for the stability and applicability of the pharmaceutical formulation.

If the surfactant/co-surfactant mixture comprises polyoxyethylene glycerol fatty acid esters and poloxamers in a mass ratio of 2:3, particularly good results could be achieved.

The formulation according to the invention contains in addition a hydrophilic phase which as is known per se from the state of the art, can comprise polyols, water or a polyol or a polyol buffer mixture or only buffer. The concentration of this component is 40-80% by weight, preferably 60-175% by weight.

A further advantageous embodiment of the invention provides, in the case of the hydrophilic phase, that a mixture of propylene glycol and water in the ratio of 1:10 to 10:1 is used. A particularly preferred mixture ratio is 2:1.

According to the invention, the pharmaceutical formulation comprises as active ingredient cyclosporin and/or a derivative thereof in a concentration of 0.1-20% by weight. It is particularly preferred if the pharmaceutical formulation comprises cyclosporin A and/or derivatives thereof. The preferred concentration is hereby in the range of 0.01-10% by weight, particularly preferred at 0.5-5% by weight.

It is of course also possible that a further active ingredient is contained in the pharmaceutical formulation in addition to cyclosporin A and/or derivatives thereof. Examples of active ingredients of this type are corticosteroids, antibiotics, antimycotics and/or virustatics.

As is known per se from the state of the art, also the normal additives, such as penetration enhancers, can be added to the pharmaceutical formulation according to the invention. If penetration enhancers are added, dimethyl sulphoxide or short-chain alcohols in a concentration of 5-10% by weight are preferred.

The pharmaceutical formulation according to the invention occurs in colloidal form. It is hereby preferred if the disperse phase has particle diameters in the order of magnitude of 5 to 200 nm. For particular preference, the particle diameters are in the dimension range of 5 to 100 nm.

The pharmaceutical formulation according to the invention is particularly suitable for the prophylaxis of inflammatory skin and mucous membrane diseases, for the therapy and prophylaxis of atopical dermatitis, for the therapy and prophylaxis of psoriasis vulgaris.

Other suitable uses are the therapy and prophylaxis of collagenoses, chronic wounds, burns and/or chronically inflammatory skin and mucous membrane diseases, and also for the therapy and prophylaxis of chronically inflammatory bowel diseases and for the therapy and prophylaxis of inflammatory diseases of the eye and after transplants.

The invention is described subsequently in more detail by means of various compositions and test results.

Composition and Production of the Vehicle Systems

Three colloidal pharmaceutical carrier systems were developed, the composition of which is evident from Table 1.

TABLE 1

Developed colloidal pharmaceutical carrier systems

|  |  | m[g] | % [w/w] |
|---|---|---|---|
| IPP-system |  |  |  |
| Cyclosporin A 2.0% (w/w) | Cyclosporin A | 0.2 | 2.0 |
| Tagat ® O2/Synperonic ® PE/L 101 2:3 20.0% (w/w) | Tagat ® O2 | 0.8 | 8.0 |
|  | Synperonic ® PE/L 101 | 1.2 | 12.0 |
| Isopropyl palmitate (IPP) 5.0% (w/w) | Isopropyl palmitate | 0.5 | 5.0 |
| Propylene glycol/water 2:1 73.0% (w/w) | Propylene glycol | 4.87 | 48.7 |
|  | water | ad 10.0 | 24.3 |
| DMSO-system |  |  |  |
| Cyclosporin A 2.0% (w/w) | Cyclosporin A | 0.2 | 2.0 |
| Tagat ® O2/Synperonic ® PE/L 121 2:3 20.0% (w/w) | Tagat ® O2 | 0.8 | 8.0 |
|  | Synperonic ® PE/L 121 | 1.2 | 12.0 |
| Oleic acid 5.0% (w/w) | Oleic acid | 0.5 | 5.0 |
| Dimethyl sulphoxide (DMSO) 5.0% (w/w) | Dimethyl sulphoxide | 0.5 | 5.0 |
| Propylene glycol/water 2:1 68.0% (w/w) | Propylene glycol | 4.53 | 45.3 |
|  | water | ad 10.0 | 22.7 |
| OA-system |  |  |  |
| Cyclosporin A 1.5% (w/w) | Cyclosporin A | 0.15 | 1.5 |
| Tagat ® O2/Synperonic ® PE/L 121 2:3 20.0% (w/w) | Tagat ® O2 | 0.8 | 8.0 |
|  | Synperonic ® PE/L 121 | 1.2 | 12.0 |
| Oleic acid 5.0% (w/w) | Oleic acid | 0.5 | 5.0 |
| Propylene glycol/water 2:1 73.5% (w/w) | Propylene glycol | 4.9 | 49.0 |
|  | water | ad 10.0 | 24.5 |

The production of the systems was effected by the concrete sequence of the following steps:
 weighing out the pharmaceutical
 addition of the surfactant/co-surfactant mixture
 thorough pulverisation
 addition of the required quantity of IPP
 thorough mixing
 addition of the produced mixture of propylene glycol and water
 agitation until becoming clear, possible short treatment of the colloidal system with ultrasound.

As emulsifiers, polyoxyethylene glycerol monooleate (Tagat® O2) and poloxamers (Synperonic® PE/L 101 or 121) were selected. For the production of the vehicle systems, a combination of both in the ratio 2:3 mass proportions proved thereby to be particularly suitable.

Mixtures of the two surfactants and of propylene glycol/water were produced in advance. Firstly, the pulverised pharmaceutical was carefully ground with the surfactant mixture and then the lipophilic phase (isopropyl palmitate or oleic acid) was added. Subsequently, the addition of the hydrophilic phase (propylene glycol/water mixture) and agitation until becoming clear was effected. DMSO was incorporated finally. If required, the systems were left for a few minutes in the ultrasonic bath.

Isopropyl palmitate or oleic acid, which both function as solvents for CsA, were used as lipophilic components. In addition, the oleic acid fulfils the function of a penetration enhancer in order to facilitate the permeation of the CsA through the stratum corneum. Dimethyl sulphoxide was added in order to improve the solubility of the CsA in the vehicle and because of its penetration-promoting properties. Polyoxyethylene glycerol monooleate, which is tolerated by human skin without reaction in a 100% concentration and is tolerated well by the mucous membrane, and also poloxamers, which are permitted for intravenous administration, were selected as surfactant/co-surfactant mixture.

Characterisation of the Vehicle Systems

The pharmaceutical carrier systems were characterised inter alia by means of dynamic laser light scattering. This method is suitable for determination of the size of colloidal particles in liquid media. Particle diameters of approximately 20 nm were able to be determined for the pharmaceutical-free formulations.

Analysis

The determination of the CsA was effected by means of an HPLC method (modified according to Merck KgaA-Darmstadt). The technical data are evident in Table 2.

TABLE 2

| Analytical data | |
| --- | --- |
| HPLC unit | Merck-Hitachi |
| | L-4250 UV-VIS Detector |
| | AS-4000A Intelligent Auto-sampler |
| | D-6000A Interface |
| | L-6200A Intelligent Pump |
| stationary phase | Lichrospher ® RP select B |
| | (Merck), 125 × 4 mm ID, 5 μm |
| mobile phase | Acetonitrile/water 70/30 (V/V) |
| flow | 1 ml/min, isocratic |
| temperature | 60° C. |
| detection | UV 210 nm |

Release Tests

By means of a multilayer membrane model system, the in vitro release of the pharmaceutical from the above-mentioned formulations was tested as a function of time.

The individual cells of the model comprise respectively a base and cover disc, between which the membrane layers were disposed. Via a gap in the cover disc (4 cm$^2$), a defined quantity of formulation (10-20 mg) was applied to the membranes. There were used as acceptor dodecanol-collodium membranes with a content of 2% dodecanol, which were produced by means of a film-drawing appliance. Via the determination of the saturation solubility of CsA in dodecanol, the absorption capacity of the acceptor was able to be determined. This is important for ensuring that achieving the saturation solubility of the pharmaceutical in the membranes is not the limiting factor of the release. By using three membranes placed one above the other, sink conditions in the acceptor were ensured.

During the duration of the test (30, 100, 300 and 1000 minutes), the model was set at a temperature of 32±1° C. After completion of the test time, the excess formulation was removed carefully, the membranes were separated, extracted with an ethanol-water mixture (80/20; V/V) and subjected to a content determination by means of HPLC. A determination was carried out five times per test time.

It can be detected from illustration 1 that all three formulations already release ~25° of the contained CsA after 30 minutes. The released pharmaceutical quantity increases in the case of longer test times. In illustration 2, for better comparison of the differently concentrated vehicles, the released pharmaceutical quantities are represented per 10 mg of applied formulation.

These tests were carried out in order to ensure that sufficient release of CsA from the vehicles is effected and hence that the prerequisite for penetration into human skin is fulfilled.

Penetration Tests

Human skin from the breast was used which was obtained by breast reduction plastic surgery. The pieces of skin, which were cut to size, were stored at −3° C. After thawing, the liquid adhering to the surface was removed with a cotton pad and the defined surface of 3.14 cm$^2$ was punched out. On the surface, approximately 6 mg of the radioactively marked test preparation was applied per cm$^2$ so that as uniform a film as possible was produced on the skin surface. Subsequently, the piece of skin lying on a gauze was stretched in the Franz diffusion cell which was set at a temperature of 32° C. The same was subjected before the beginning of the test in the filled state to a thirty minute equilibration phase. The acceptor medium, which was constantly agitated in order to reduce the diffusion layer thickness, abutted directly against the underside of the skin or the gauze. In order to simulate physiological conditions, isotonic NaCl solution was used as acceptor liquid. The tests were carried out respectively on three different operation preparations as threefold determinations. After completion of the action duration, the pieces of skin were removed and fixed on a styropore box covered with aluminium foil by means of pins. Subsequently, the test preparation was wiped off with a gauze swab.

The removal of the stratum corneum was effected through a template which contained a circular gap (d=16 mm). Through this gap, 20 Tesa film strips (Tesa Film® 4 204, 33 m×19 mm; Co. Beiersdorf AG, Hamburg) were removed from a 2.0106 cm$^2$ skin surface. Two successively obtained strips respectively were measured together.

From the remaining piece of skin, by means of a Kromayer punch (diameter 6 mm; Stiefel Laboratorium GmbH, Offenbach), three cylinders with a total surface of 0.848 cm$^2$ were punched out approximately from the centre of the skin area. With a freezing microtome, the thus obtained cylinders of tissue were successively deep-frozen to −40° C. and cut horizontally relative to the skin surface. 10×20 μm sections were thereby removed in order to remove the vital epidermis components and 15×80 μm sections for processing the corium. Thereafter, a corium residue (stump) and the acceptor medium were left over.

It is evident from the illustrations 3-5 that, in the case of all three formulations, after just 30 minutes>25% (IPP 35%, OA 32%, DMSO 27%) of the contained CsA penetrated into the acceptor. In the case of longer test times, the penetrated pharmaceutical quantity is increased slightly. In the illustrations 6-8, for better comparison of the differently concentrated vehicles, the penetrated pharmaceutical quantities are represented in μg.

The previously published galenic data of cyclosporin-containing preparations for topical application reveal an inadequate release and/or penetration of the effective substance. Hydrophilic and lipophilic standard systems or liposomal formulations were thereby tested. In many cases, there are no exact indications in the publications with respect to the contents of the used preparations, the type of production or the galenic data. Two reasons are indicated for the non-occurring clinical effect. Firstly, because of the strong lipophily of CsA, a too low release and/or penetration of the active ingredient into the corial layers of the skin is assumed. Secondly, a significantly penetration-inhibiting factor is observed in the high molar mass. The present results reveal firstly release and penetration rates of approximately 25-30% of the applied active ingredient concentration in the first 30 to 100 minutes on healthy, i.e. barrier-intact skin ex vivo. Fundamentally, on a skin lesion (e.g. psoriasis plague) more favourable penetrable conditions can be assumed in comparison to healthy skin.

Topical application of CsA, in comparison to systemic therapy, produces significant advantages. In the case of topical application, even in the case of large-area treatment, minimal and non-clinically relevant systemic side effects must be taken into account. The known undesired pharmaceutical effects, in particular kidney function disturbance and arterial hypertonia, should not be expected or only to a lesser extent. Use can be possible even for patients who have already developed side effects due to a systemic therapy and therefore who are no longer treated with CsA. In addition, due to topical application, an increased spectrum of effectiveness is produced. In a multiplicity of inflammatory dermatoses, the formation and effect of nitrogen monoxide (NO), which is formed from L-arginine by the enzyme NO synthesis, is central to the pathogenesis. The most recent research results reveal that the causation and maintenance of the inflammation in the case of psoriasis is substantially occasioned by NO. CsA is, as is known, a sufficient blocker of NOS which is present also in dermal microvascular endothelial cells due to the isoenzymes eNOS and iNOS and is inhibited by a high tissue concentration of CsA after topical application to a greater extent than after systemic application. In addition, CsA also has a proliferation-inhibiting effect on keratinocytes which synergistically influences the effect on skin psoriasis in the case of topical application. A cost reduction per case due to the smaller required quantity of CsA would also be favourable.

Disadvantages of topical application and of the therewith connected reduced system concentration are above all observed in the non-occurring effect on the lymph nodes in which substantial activation processes take place at a T-cell level. In addition, a therapeutic effect on psoriasis arthropathica should not be expected.

The present tests prove firstly that it is possible to develop a galenic system which fulfils the preconditions for penetration of CsA in sufficient concentration into the upper corium layers. Stable vehicle systems are present into which CsA can be incorporated adequately. The loading of the system has intentionally been chosen to be very high in order to exhaust the galenic properties of the systems and to produce favourable preconditions for clinical application. Smaller CsA concentrations can be achieved without difficulty with sufficient clinical effectiveness. The release tests prove that, in a relevant time, pharmaceutical quantities between 25 and 40% are released and are available for penetration into the skin.

The penetration tests under ex vivo conditions have proved of decisive importance for preclinical development. They make it clear that, after a relevant application duration (30-100 min), penetration of approximately 25-30% of the active ingredient concentration into or respectively through the corial layers is effected and hence is available at the desired effective site.

The contents of the preparations were selected according to dermatological viewpoints. No highly potent sensitising substances are contained and self tests have shown good tolerability, which make an irritative or toxic effect appear very improbable even in the case of barrier function disorders in various dermatoses. As main indication fields, there are psoriasis vulgaris of the chronically stationary type or atopical dermatitis. In addition, a multiplicity of possible indications are produced connected to systemic therapy. In particular the use in collagenoses, burns, skin or mucous membrane transplants and chronic wounds is considered possible.

The application of the systems is not only provided for the outer skin. Basically, the possibility exists also of application to the eye after corneal transplant or for the therapy of cicatricial mucous membrane pemphigoid or application in the oral mucous membrane area in the case of lichen ruber mucosae or as clyster in the case of chronically inflammatory bowel diseases (e.g. M. Crohn, colitis ulcerosa) if necessary also by intraluminal foaming.

The invention claimed is:

1. A method of treatment of inflammatory skin and mucous membrane diseases, comprising the step of topical application of a pharmaceutical formulation in colloidal form to a patient, said pharmaceutical formulation comprising:
    a) a lipophilic phase in a quantity of 1-10% by weight,
    b) a mixture of surfactant, wherein the surfactant comprises polyoxyethylene glycerol fatty acid esters, and co-surfactant, wherein the co-surfactant comprises poloxamers in a quantity of 1-50% by weight, the surfactant/co-surfactant mixture being used in a mass ratio of 2 for the surfactant and 3 for the co-surfactant,
    c) a hydrophilic phase in a quantity of 40-80% by weight, and
    d) as active ingredient, cyclosporin, in a concentration of 0.1-20% by weight.

2. A method of treatment of atopical dermatitis, comprising the step of topical application of a pharmaceutical formulation in colloidal form to a patient, said pharmaceutical formulation comprising:
    a) a lipophilic phase in a quantity of 1-10% by weight,
    b) a mixture of surfactant, wherein the surfactant comprises polyoxyethylene glycerol fatty acid esters, and co-surfactant, wherein the co-surfactant comprises poloxamers in a quantity of 1-50% by weight, the surfactant/co-surfactant mixture being used in a mass ratio of 2 for the surfactant and 3 for the co-surfactant,
    c) a hydrophilic phase in a quantity of 40-80% by weight, and
    d) as active ingredient, cyclosporin, in a concentration of 0.1-20% by weight.

3. A method of treatment of psoriasis vulgaris, comprising the step of topical application of a pharmaceutical formulation in colloidal form to a patient, said pharmaceutical formulation comprising:
    a) a lipophilic phase in a quantity of 1-10% by weight,
    b) a mixture of surfactant, wherein the surfactant comprises polyoxyethylene glycerol fatty acid esters, and co-surfactant, wherein the co-surfactant comprises poloxamers in a quantity of 1-50% by weight, the surfactant/co-surfactant mixture being used in a mass ratio of 2 for the surfactant and 3 for the co-surfactant,
    c) a hydrophilic phase in a quantity of 40-80% by weight, and
    d) as active ingredient, cyclosporin, in a concentration of 0.1-20% by weight.

4. A method of treatment of collagenoses, chronic wounds, burns, and/or chronically inflammatory skin and mucous membrane diseases, comprising the step of topical application of a pharmaceutical formulation in colloidal form to a patient, said pharmaceutical formulation comprising:
   a) a lipophilic phase in a quantity of 1-10% by weight,
   b) a mixture of surfactant, wherein the surfactant is comprises polyoxyethylene glycerol fatty acid esters, and co-surfactant, wherein the co-surfactant comprises poloxamers in a quantity of 1-50% by weight, the surfactant/co-surfactant mixture being used in a mass ratio of 2 for the surfactant and 3 for the co-surfactant,
   c) a hydrophilic phase in a quantity of 40-80% by weight, and
   d) as active ingredient, cyclosporin, in a concentration of 0.1-20% by weight.

5. A method of treatment of chronically inflammatory bowel disease, comprising the step of application of a pharmaceutical formulation in colloidal form to a patient as a clyster, said pharmaceutical formulation comprising:
   a) a lipophilic phase in a quantity of 1-10% by weight,
   b) a mixture of surfactant, wherein the surfactant comprises polyoxyethylene glycerol fatty acid esters, and co-surfactant, wherein the co-surfactant comprises poloxamers in a quantity of 1-50% by weight, the surfactant/co-surfactant mixture being used in a mass ratio of 2 for the surfactant and 3 for the co-surfactant,
   c) a hydrophilic phase in a quantity of 40-80% by weight, and
   d) as active ingredient, cyclosporin, in a concentration of 0.1-20% by weight.

6. A method of treatment of inflammatory diseases of the eye, comprising the step of topical application of a pharmaceutical formulation in colloidal form to a patient, said pharmaceutical formulation comprising:
   a) a lipophilic phase in a quantity of 1-10% by weight,
   b) a mixture of surfactant, wherein the surfactant comprises polyoxyethylene glycerol fatty acid esters, and co-surfactant, wherein the co-surfactant comprises poloxamers in a quantity of 1-50% by weight, the surfactant/co-surfactant mixture being used in a mass ratio of 2 for the surfactant and 3 for the co-surfactant,
   c) a hydrophilic phase in a quantity of 40-80% by weight, and
   d) as active ingredient, cyclosporin, in a concentration of 0.1-20% by weight.

7. A method of treatment of rejection reactions after transplants, comprising the step of topical application of a pharmaceutical formulation in colloidal form to a patient, said pharmaceutical formulation comprising:
   a) a lipophilic phase in a quantity of 1-10% by weight,
   b) a mixture of surfactant, wherein the surfactant comprises polyoxyethylene glycerol fatty acid esters, and co-surfactant, wherein the co-surfactant comprises poloxamers in a quantity of 1-50% by weight, the surfactant/co-surfactant mixture being used in a mass ratio of 2 for the surfactant and 3 for the co-surfactant,
   c) a hydrophilic phase in a quantity of 40-80% by weight, and
   d) as active ingredient, cyclosporin, in a concentration of 0.1-20% by weight.

* * * * *